United States Patent [19]
Bobo, Jr.

[11] Patent Number: 4,959,050
[45] Date of Patent: Sep. 25, 1990

[54] IN-LINE INFILTRATION DETECTION APPARATUS AND METHOD

[75] Inventor: Donald E. Bobo, Jr., Orange, Calif.

[73] Assignee: Baxter International Inc., Deerfield, Ill.

[21] Appl. No.: 249,065

[22] Filed: Sep. 26, 1988

[51] Int. Cl.$^5$ ............................................. A61M 5/00
[52] U.S. Cl. ........................................ 604/49; 604/67; 128/DIG. 13
[58] Field of Search ............................. 604/50, 65–67, 604/118, 245, 246; 128/DIG. 12, DIG. 13, 748, 681

[56] References Cited

U.S. PATENT DOCUMENTS

| | | | |
|---|---|---|---|
| 3,690,318 | 9/1972 | Gorsuch et al. | 604/141 |
| 4,140,110 | 2/1979 | Jansen et al. | 128/681 |
| 4,392,847 | 7/1983 | Whitney | 604/118 |
| 4,468,219 | 8/1984 | Georges et al. | 604/66 |
| 4,648,869 | 3/1987 | Bobo, Jr. | 604/49 |
| 4,657,529 | 4/1987 | Prince et al. | 604/6 |
| 4,710,163 | 12/1987 | Butterfield | 604/65 |

FOREIGN PATENT DOCUMENTS

| | | |
|---|---|---|
| 0121931 | 10/1984 | European Pat. Off. . |
| 0248632 | 9/1987 | European Pat. Off. . |
| 0248633 | 9/1987 | European Pat. Off. . |
| 8705224 | 9/1987 | European Pat. Off. . |

Primary Examiner—Stephen C. Pellegrino
Attorney, Agent, or Firm—Paul E. Schaafsma; Debra E. Dahl; Paul C. Flattery

[57] ABSTRACT

The present invention provides a stand-alone, in-line device and method for detecting whether a fluid is being properly supplied to a patient, including means for delivering a test pulse of the fluid through conduit means to the patient with the test pulse being distinguishable from the normal delivery pattern and with the test pulse creating a pressure wave response in the conduit means. The device and method also includes means for determining the area between a baseline and at least a portion of a pressure versus time curve representing the pressure wave response, and means responsive to the magnitude of the area for detecting whether the fluid is being improperly supplied by the conduit means to the patient. Preferably, the device and method also includes means for diverting and accumulating a predetermined volume of the upstream flow from the infusion source for use as the test pulse.

53 Claims, 7 Drawing Sheets

IN-LINE INFILTRATION DETECTION APPARATUS AND METHOD

This is a continuation-in-part of U.S. Pat. application Ser. No. 165,619 entitled Automatic Infiltration Detection System and Method, filed Mar. 8, 1988 now U.S. Pat. No. 4,846,292.

FIELD OF INVENTION

In general, the present invention relates to an apparatus and method for detecting abnormal infusion of a fluid being supplied to a patient, and specifically, to an apparatus and method for detecting whether infiltration of the fluid into the tissue at the IV site has occurred.

BACKGROUND OF THE INVENTION

It is often necessary or desirable to infuse a flowable material or fluid, which may be a liquid, a gas or a combination thereof, into the vascular system of a patient. One example is the administration of parenteral fluids to a patient.

A typical infusion system includes an infusion device for delivering the fluid and conduit means for conducting the fluid from the infusion device to the patient. The conduit means typically comprises flexible tubing leading from the infusion device to the patient and a cannula, such as a needle or catheter, for insertion into the vascular system of the patient. In normal operation, the infusion device delivers the fluid through the tubing and the needle to the vascular system of the patient.

One problem with infusion systems of this type is a condition known as infiltration. Infiltration is a condition in which infused fluid finds its way into extravascular tissues rather than simply being released into the blood stream. Such a situation occurs when the needle is not in communication with the interior of the vessel into which the fluid is to be infused. When this occurs, fluid is infused into the interstitial spaces between layers of tissues. Thus, the patient is deprived of proper intravenous drug administration and is further subjected to possible toxic or caustic effects associated with infused fluids being in direct contact with body tissues.

Infiltration is not the only possible type of anomaly associated with intravenous therapy which can cause the fluid to be improperly supplied to the patient. Other conditions which can cause abnormal infusion include venous inflammation and swelling at the infusion site (phlebitis), clotting, and a wide variety of obstructions of the conduit means, such as kinking of the tubing which supplies the fluid to the patient. Many of these affect fluid flow characteristics in a manner similar to infiltration and can, therefore, be detected by infiltration detection devices.

The goal of an infiltration detection system is to identify an abnormal infusion as early as possible without generating an excessive number of false alarms. Early detection allows the attending medical staff to rectify the problem before significant tissue damage has been done by the infiltration and before the patient has been deprived of a significant amount of the intravenous therapy. On the other hand, if the detection system is too sensitive, false alarms will result. This is very undesirable since, from a clinical perspective, establishing a new intravenous site can be difficult and time consuming. During the time necessary to start the new IV, which can be hours in some cases, the patient is not receiving the desired treatment.

Bobo U.S. Pat. No. 4,648,869 discloses a significant advance in the field of infiltration detection systems and methods. According to the Bobo patent, an infusion system infuses a test pulse or rate pulse of fluid to a patient. The test pulse creates a pressure wave response in the conduit which can be monitored and used to detect whether abnormal infusion has occurred.

Butterfield U.S. Pat. No. 4,710,163 discloses an infusion system which uses the test pulse-pressure wave response concept of the Bobo patent. However, the Butterfield system compares the test pulse pressure wave response with a reference pressure wave response which represents the normal response when there is no infiltration. Specifically, the area between the two curves representing these responses is used to attempt to detect infiltration. Thus, the Butterfield approach has the disadvantage of requiring that a normal pressure wave response be first determined and then stored for later comparison.

Bobo et al. copending Pat. application, Ser. No. 165,619, entitled Automatic Infiltration Detection System and Method, filed Mar. 8, 1988, utilizes the test pulse-pressure wave response concept of the Bobo '869 patent, but to determine whether abnormal infusion is occurring, Bobo utilizes the area between a baseline and at least a portion of a pressure versus time curve which represents the test pulse pressure wave response. With this technique, it is not necessary to first establish a normal pressure wave response for a patient, nor is it necessary to compare the assumed normal response to the test pulse pressure wave response. Rather, all that is required to make accurate determinations as to the proper supply of fluid to a patient is appropriate area information from the test pulse pressure wave response.

All of the infiltration detection systems known in the art and those described in the Bobo patent and copending patent application, involve a monitoring or detection system incorporated into some type of infusion control device, such as a pump or controller. The infusion device is then programmed or controlled to deliver a test pulse and to monitor the pressure-wave response in the conduit line to the patient, as well as supply the fluid to the patient in the normal or selected delivery pattern.

There is a need for an infiltration detection system that is independent of the infusion device and that can be used with any manufacturer's IV control device, as well as a gravity controlled infusion system, and eliminates the need for hospitals to replace existing infusion pumps with new infusion pumps capable of detecting infiltration.

It is therefore an object of the present invention to provide a stand-alone, in-line infiltration detection device that is small, lightweight, and capable of implementing the rate pulse technology without the complexities and expense of an infusion pump or device.

It is another object of the present invention to provide a stand-alone, in-line infiltration detection system that is compatible with any manufacturer's infusion pump or device, as well as gravity controlled infusion systems.

It is another object of the present invention to eliminate the problems associated with height differences between the pressure transducer and the patient's IV site, by providing a stand-alone, in-line infiltration detection device that may be placed in close proximity to the IV site.

It is a further object of the present invention to provide a stand-alone, in-line infiltration detection system that delivers a test pulse without the noise caused by background flow in an infusion pump, thereby providing a quieter environment for the test pulse stimulus, resulting in less noise and therefore improved signal discrimination.

SUMMARY OF THE INVENTION

The present invention provides a stand-alone, in-line detection device and method for detecting abnormal infusion, and specifically, for detecting whether infiltration of the fluid into the tissue at the IV site has occurred. The flow of the fluid from the infusion source is controlled by an infusion control device, such as a pump, or by a gravity controlled infusion system (hereinafter collectively referred to as the "flow controller"). The flow controller delivers fluid to the patient in a normal delivery pattern at any of a plurality of selected infusion rates through conduit means.

The detection device and method of the present invention include means for delivering a test pulse of the fluid through the conduit means to the patient with the test pulse being distinguishable from the normal delivery pattern of the flow controller and with the test pulse creating a pressure wave response in the conduit means. Preferably, the detection device and method also include means for diverting and accumulating a predetermined volume of the upstream flow from the flow controller for use as the test pulse.

The detection device and method of the present invention also include means for determining the area between a baseline and at least a portion of a pressure versus time curve representing the pressure wave response to the test pulse, and means responsive to the magnitude of the area for detecting whether the fluid is being improperly supplied by the conduit means to the patient. The area information needed to determine whether a fluid is being improperly supplied to a patient can be obtained in accordance with the teachings of Bobo's copending U.S. Pat. application, Ser. No. 165,619, filed Mar. 8, 1988, which is incorporated by reference herein.

Specifically, the pressure wave response has a peak value of pressure and a leading portion and a trailing portion on opposite sides of the peak value. When fluid is being properly supplied to the patient, the pressure will rise rapidly but typically not to a very high peak value. However, if the fluid is being improperly supplied to the patient as when infiltration occurs, the pressure will rise to a higher peak value over a longer period of time. The peak pressure is large because the infused fluid has no immediate means of escape from the interstitial spaces. After termination of the test pulse, the pressure will drop rapidly to its nominal level if the fluid is being properly supplied to the patient. In the case of abnormal infusion, the pressure drops much more slowly from the peak value because there is no immediate escape path for the fluid.

The integration technique of this invention and of Bobo's copending patent application uses an area characteristic of the pressure wave response to determine if fluid is being improperly supplied to the patient. The function integrated is the difference between a baseline and a curve representing the test pulse pressure wave response and extends along the curve from an initial point to a truncation point. Although the baseline can be established in different ways, preferably, the baseline is established as a function of the pressure in the delivery system when the test pulse and, hence the pressure wave response, are not present. The baseline used for the integration is preferably held essentially constant during the integration.

The initial point, or lower limit on the integration, is preferably essentially at the beginning of the point on the curve corresponding to the beginning of the pressure wave response. The truncation point, or upper limit on the integration, preferably is on the trailing portion of the curve corresponding to the trailing portion of the pressure wave response, i.e., after the peak value of pressure has been attained. Although it is possible to truncate the integration prior to or at the peak value of pressure, because the peak pressure is typically drastically different when the fluid is being improperly supplied to the patient, it is highly desirable to include, and go beyond, the peak value for the integration.

The output from a flow controller used to deliver the fluid to the patient may not be totally uniform, and preferably, the truncation point occurs at a time which is sufficiently beyond the peak value of pressure so as to take this into account. Typically, it is preferred that the truncation point be at a time at which the pressure is no greater than about 70 percent of the peak value.

On the other hand, the truncation point is preferably essentially outside of the noise range, and this typically means that it occurs at a time at which the pressure is no less than about 30 percent of the peak value. Thus, the truncation point is preferably at a time at which the pressure is between about 30 percent and about 70 percent of the peak value with about 50 percent being considered optimum.

Alternatively, or in addition thereto, the integration of the pressure wave response may extend from the initial point to about the peak value of pressure. Such an integration would determine a front end area. The detecting means may be responsive to either or both of the front end area and the truncated area. Preferably, the detecting means is responsive to both of these areas.

The detection device should be capable of delivering a test pulse of the fluid to create a pressure wave response in the delivery system. Typically, to accomplish this, the test pulse must be distinguishable from the normal delivery pattern of the infusion source. The flow rate during the test pulse may be less than, greater than, or equal to the flow rate during the normal delivery pattern. It is also possible to reverse the flow in the delivery system to create a negative test pulse, however, this is not preferred because it may cause the patient's vessel to collapse around the needle.

The test pulse can be distinguished from the normal delivery pattern in different ways. Preferably, the test pulse is separated from the normal delivery pattern by separating regions on one or both sides of the test pulse, with each of the separating regions providing a different flow rate of fluid than the adjacent portions of the test pulse. The separating regions may have flow rates equal to or greater than the flow rate of the normal delivery pattern, but preferably, have reduced flow rates or flow rates of essentially zero, providing an altered pattern of flow which includes leading and trailing valleys on opposite sides of the test pulse.

In a preferred embodiment, the present invention alters the fluid flow pattern by diverting and accumulating the flow from the flow controller, and then utilizes the accumulated flow to deliver a test pulse having a greater flow rate than the normal delivery pattern. In this embodiment, the detection device also regulates the fluid flow to provide a period of reduced flow or no flow just prior to and following the test pulse.

When this form of infusion is used, the truncation point is preferably established as the first to occur of a specified percent of peak value and the termination of the trailing valley. This is desirable because, in the case of infiltration, where the pressure wave response decays slowly, the predetermined percent of peak value may not be reached. With this form of infusion, the initial point may coincide with the beginning of the test pulse.

The preferred altered pattern, as described above, has several advantages, including the advantage of preventing the test pulse from significantly altering the average flow of fluid to the patient. Moreover, by diverting and accumulating the fluid flow from the flow controller and utilizing the accumulated fluid as the next pulse in accordance with the present invention, the average flow of fluid to the patient should not be altered at all. The patient receives all of the fluid that would have been received had the normal delivery pattern been unaltered.

The area information from the test pulse can be processed in various different ways to determine if the fluid is being properly or improperly supplied to the patient. Generally, a larger area indicates an alarm condition, and a smaller area is indicative of normal infusion. The areas are also a function of test pulse infusion rates. Of course, information from multiple pressure wave responses derived from multiple test pulses can be processed to gain greater assurance that the infusion system is being correctly monitored.

Another important feature of this invention is ascertaining if the pressure conditions in the conduit are suitable for detecting abnormal infusion. It has been found that the occurrence of a baseline pressure during the normal delivery pattern which is unusually large in magnitude or which fluctuates excessively, suggests that the pressure conditions in the conduit are not then suitable for detecting abnormal infusion. Such baseline conditions could be the result of a transient condition, such as movement by the patient. Because the present invention provides a lightweight stand-alone, in-line device that can be placed in close proximity to the IV site, preferably, adjacent to the IV site on the patient's arm, pressure artifacts caused by patient movement can be virtually eliminated. However, in some cases it may not be possible to mount the device adjacent to the IV site, for example, if the patient is an infant.

If pressure artifacts occur, either the application of the test pulse is deferred or the data derived from such test pulse is ignored. One reason for this is that these pressure artifacts would be superimposed upon the pressure wave response. This would tend to unacceptably alter the pressure wave response such that the pressure wave response would not be indicative of the health of the IV site, but rather indicative of some other condition, such as unusual patient movement.

The suitability of the pressure conditions in the conduit can be determined in accordance with the method taught in Bobo's copending application, that is, by comparing a function of the pressure of the fluid in the conduit during the normal delivery pattern to a threshold. This function of the pressure may be one or more pressure values or may be a function which is derived from sampling and averaging one or more pressure values. In a preferred technique, the function of the pressure equals $B1+K(B2)$, where $B1$ is the baseline pressure at an instant prior to the test pulse, $K$ is a constant, and $B2$ is the rms value of a plurality of segments of the baseline pressure prior to the test pulse, with at least one of the segments being prior to such instant.

The suitability of the pressure conditions in the conduit can also be determined by providing a waiting period or quiet period just prior to delivering the test pulse. The waiting period or quiet period is a period of reduced or no flow of fluid prior to delivery of the test pulse. This can be accomplished by controlling the flow rate of the fluid via the flow controller or preferably, the detection device itself stops or reduces the flow from the flow controller by diverting and accumulating the flow prior to the test pulse. The waiting period of reduced or no flow permits the baseline to stabilize prior to delivering the test pulse and will ensure a more accurate area determination.

Because the detection apparatus of the present invention is a stand-alone device that is independent of the infusion pump or device, it can deliver a test pulse in a much quieter environment. This is because when an infusion device delivers a test pulse, the background flow in the device creates noise that can interfere with the test pulse signal. The present invention diverts or stops the background flow from the infusion device prior to and during delivery of a test pulse, thus there is much less noise to interfere with the test pulse stimulus and to distort the pressure wave response. Better discrimination of the signal and more accurate area determinations result.

The invention, together with additional features and advantages thereof, may best be understood by reference to the following detailed description of the invention taken in conjunction with the accompanying drawings.

DETAILED DESCRIPTION OF THE INVENTION

Figure 1:
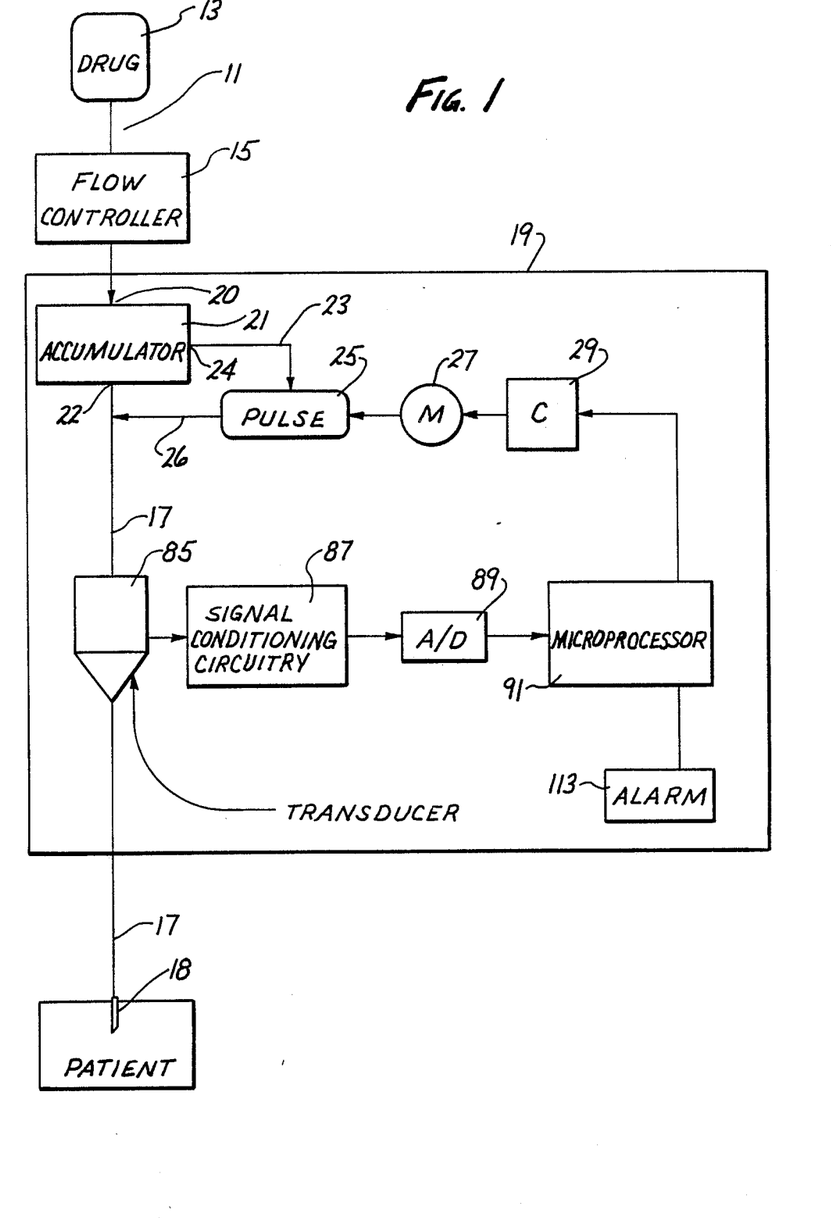
FIG. 1 is a block diagram illustrating one preferred embodiment of an infiltration detection system constructed in accordance with the teachings of this invention.

FIG. 1 shows an infusion system 11 which comprises a source 13 of a parenteral fluid, an infusion device or flow controller 15 for delivering the parenteral fluid through conduit means 17 to a patient. The conduit means 17 may comprise flexible tubing or other flow channels for supplying the parenteral fluid to the patient. The conduit means terminates in a needle 18, such as an I.V. needle, which is adapted to be inserted into a vessel of the patient's vascular system so that the open distal end of the needle communicates with the interior of the vessel. In this embodiment, the needle 18 is inserted into a vein. If the open distal end of the needle communicates with tissue, as when the needle is forced completely through the vessel wall, infiltration has occurred.

The infusion device or flow controller 15 may be an infusion pump, an infusion control device, a gravity controlled infusion system, a syringe, or the like, which is capable of delivering the fluid in a normal delivery pattern at any of a plurality of selected infusion rates. Preferably, the infusion device or flow controller has a normal delivery pattern that is essentially constant.

Figure 3:
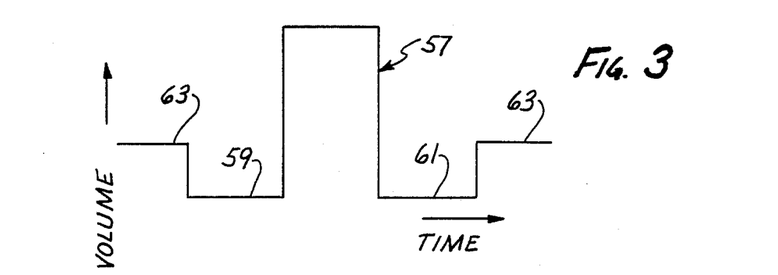
FIGS. 3-3E are plots of volume versus time, illustrating different examples of test pulses.

In a preferred construction, the infusion device 15 is a peristaltic pump of the type disclosed in application Ser. No. 661,032 entitled Continuous Delivery Peristaltic Pump and filed on Oct. 15, 1984. Such an infusion pump has a normal delivery pattern 63 which, in this example, is essentially constant as shown by the flat portions of the pump delivery curve of FIG. 3. This is the result of accelerating through the deadband of the peristaltic pump. The curve of FIG. 3 is somewhat idealized in that the preferred infusion pump provides periodic short spikes and valleys of exceedingly short duration, however, these are sufficiently insignificant so that the normal delivery pattern of the pump can be considered as essentially constant. A constant flow rate during the normal delivery pattern is preferred but not required.

The infiltration detection device 19 is a stand-alone, in-line device which in a preferred embodiment comprises an accumulator 21 that accumulates fluid flow from the flow controller for use as a test pulse. Three valves (not shown) cooperate with the accumulator 21 to regulate the fluid flow into an out of the accumulator 21.

A valve at the inlet 20 of the accumulator 21 is opened during the normal delivery pattern and during the accumulation period to permit the accumulator 21 to begin collecting fluid in a reservoir (not shown) for use as a test pulse. Accumulation takes place during normal delivery or during the waiting period preceding a test pulse. A valve at the outlet 22 regulates the flow rate through the outlet of the accumulator 21. Preferably, a period of reduced or no flow is provided prior to and after delivering each test pulse. This waiting period or quiet period ensures that the baseline is stabilized prior to delivering a test pulse. Preferably, the waiting period is about 3-5 seconds, more preferably 4 seconds, but can be any short length of time, and depends in part on the volume of fluid desired for the test pulse, if accumulation occurs during the waiting period.

When the predetermined or desired volume of fluid has been accumulated, the valve at outlet 24 is opened to deliver the accumulated fluid through conduit 23 to pulse generator 25 which is driven by motor 27 to deliver a test pulse. Preferably, motor 27 is battery operated so that the infiltration detection device is entirely self-contained. The motor 27 is controlled by controller 29 which can be programmed to direct the pulse generator to deliver test pulses at specified intervals, and at any time upon demand by the operator of the device. The pulse generator delivers the test pulse as directed by controller 29 through conduit 26 to conduit 17.

Preferably, the accumulator accumulates a volume of fluid sufficient to deliver three test pulses, i.e., a triple rate pulse, and the pulse generator delivers the three test pulses in rapid succession with a waiting period between each pulse and following the third pulse.

Preferably, the inlet valve is closed during the quiet period to eliminate noise resulting from the background flow of fluid from the flow controller. In that case, accumulation takes place during the normal delivery pattern. Although it is preferred that the flow rate during the quiet period is essentially zero, in some cases it may be desirable to provide a reduced flow which in the case of the inlet valve being closed would be accomplished by utilizing a portion of the accumulated flow. The reduced flow could then be provided through the valve at outlet 22 by retaining a portion of the accumulated flow in the accumulator when the test pulse volume is delivered to the pulse generator, or could be provided by the pulse generator, for example, by controlling the speed of a plunger to deliver a reduced flow rate, a test pulse, a reduced flow rate, until the desired number of pulses are delivered.

If the flow rate is to be stopped completely during the waiting period, accumulation can occur during the waiting period by closing the valve at outlet 22, accumulating the desired volume and delivering it to the pulse generator, then closing the inlet valve to eliminate the background noise from the flow controller, and delivering the test pulse or sequence of test pulses. In this case, the plunger can be controlled to deliver a test pulse, stop for a quiet period, deliver a test pulse, stop, deliver, stop. To resume normal flow the inlet valve and the outlet valve at 22 are opened.

Figure 2:
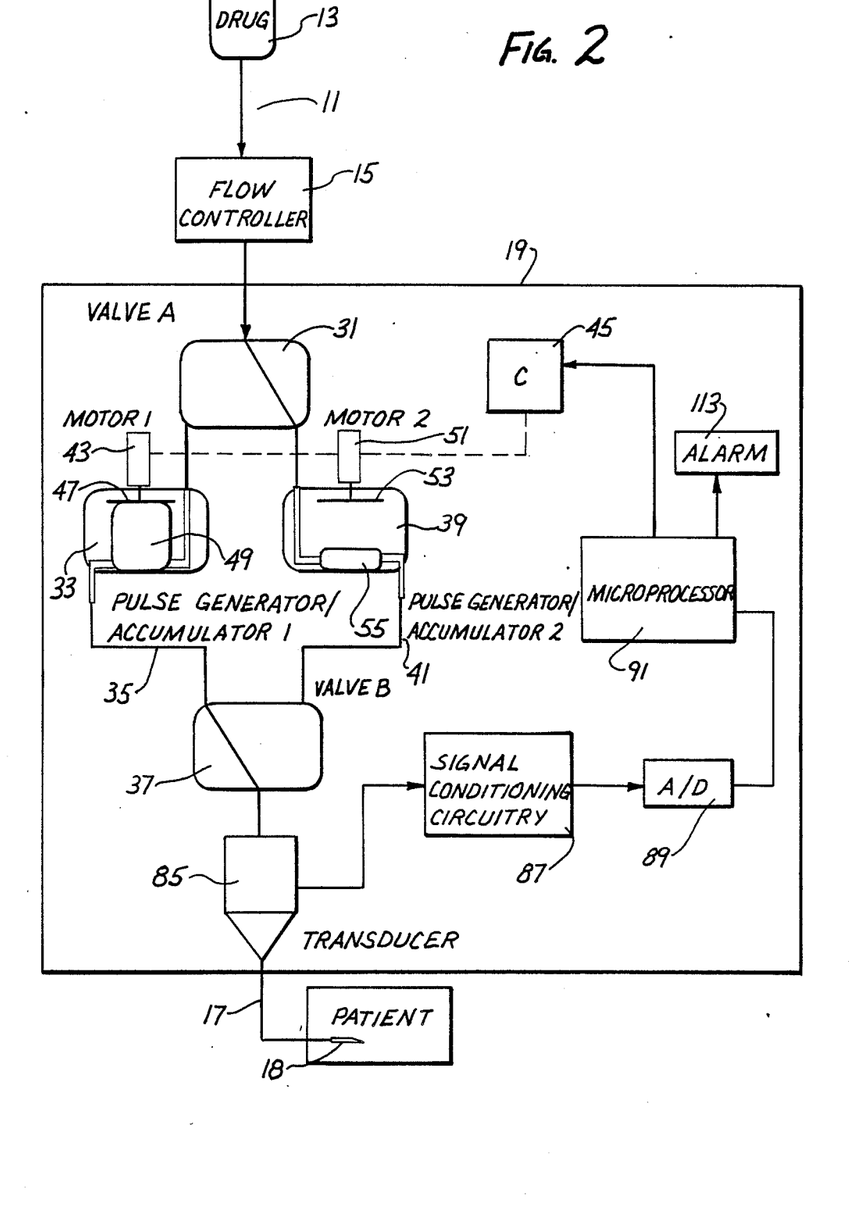
FIG. 2 is a block diagram illustrating another preferred embodiment of an infiltration detection system constructed in accordance with the teachings of this invention.

FIG. 2 shows another preferred embodiment of the infiltration detection system of the present invention which differs from the embodiment disclosed in FIG. 1 in that their are two accumulators, each with a respective pulse generator. Specifically, there is a source of parenteral fluid 13, a flow controller 15 for controlling the flow of fluid to the patient. The fluid is delivered to the patient through conduit means 17 which terminates in a needle 18, adapted to be inserted into a vessel of the patient's vascular system.

The infiltration detection device 19 includes a two way valve 31 which directs the fluid flow to the first accumulator 33 or the second accumulator 39 depending on which accumulator is collecting fluid and which accumulator is delivering a test pulse. Prior to start up of infusion to the patient, valve 31 opens to accumulator 33 and two way valve 37 closes the flow pathway 35 leading from accumulator 33, so that the desired volume of fluid for a test pulse or a series of test pulses can be collected in reservoir 49.

When the first accumulator 33 is full, valve 31 closes the conduit pathway to the first accumulator and opens the conduit pathway to the second accumulator 39, and valve 37 closes the conduit pathway 35 and opens the conduit pathway 41. At this point infusion to the patient begins at the desired infusion rate in a normal delivery pattern. During normal delivery, the plunger 53 of motor 51 is pressed against the reservoir 55 to prevent accumulation and to provide a flow-through passageway with a diameter closer to the diameter of conduit 41.

When the time comes to deliver a test pulse at the predetermined intervals or on demand, valve 37 closes the pathway between conduit 41 and conduit 17 and opens the pathway between conduit 35 and conduit 17. Valve 31 remains open to the second accumulator so that while the first accumulator delivers a test pulse or a series of test pulses, the second accumulator collects the desired volume of fluid in reservoir 55 for delivering the next test pulse or series of test pulses.

After a waiting period of approximately 3 to 5 seconds, preferably, 4 seconds, the first motor 43 which is controlled by controller 45, drives the plunger 47 against the reservoir 49 to deliver a test pulse or a series of test pulses, preferably three, to conduit 17 and the patient. Following the test pulse, there is another 3 to 5 second waiting period, preferably 4 seconds. Preferably, as described in FIG. 1, the accumulator 33 delivers a series of three test pulses in rapid succession with a waiting period between each test pulse. The speed of plunger 47 can be controlled to provide increased flow, reduced flow or no flow prior to and following each test pulse, preferably, reduced flow or no flow, as described above with reference to FIG. 1.

Alternately, the first accumulator can deliver one test pulse while the second accumulator collects fluid, the second accumulator can provide the next pulse while the first accumulator collects fluid, and the first accumulator can provide the third test pulse while the second accumulator collects fluid. The three pulses would be delivered in rapid succession with each accumulator providing the desired waiting period on either side of the test pulse it delivers. Although a triple rate pulse is preferred, a single rate pulse or a series of more than three rate pulses can be effective as well.

While it is preferred that accumulation by one accumulator occur during delivery or the test pulse or series of test pulses by the other accumulator, it is possible that in some cases the selected infusion rate may be too slow to provide the desired volume during the time allowed. In that case, additional volume can be collected from background flow during the normal delivery pattern. In other words, when accumulator 33 finishes delivering the test pulse, valve 31 remains open to accumulator 39 and valve 37 closes flow path 35 from the first accumulator and opens flow path 41. Normal delivery therefore resumes through the second accumulator 39 and a portion of the background flow is collected until the desired volume has been obtained.

When the time comes to deliver the next pulse, valve 31 switches back to the first accumulator 33 and the second accumulator 39 delivers its test pulse while accumulator 33 begins collecting fluid. Normal delivery is then resumed through accumulator 33 by switching valve 37 back to the first accumulator. The accumulation then continues through the normal delivery pattern until the desired volume has been collected.

It is also possible that the infusion rate from the flow controller will be faster than needed to collect the desired volume in the second accumulator during the time the first accumulator is delivering a test pulse. In that case, the additional volume collected can be leaked out immediately following delivery of the rate pulse by the second accumulator. Alternately, the additional volume can be leaked out during the waiting period prior to and following delivery of the rate pulses, as opposed to providing a period of no flow between the rate pulses. It is preferred, of course, that the infusion rate and volume of fluid required for the test pulse be coordinated so that only the required volume is collected.

In the preferred embodiment shown in FIG. 2, accumulator 39 collects the required volume for the next triple rate pulse while accumulator 33 delivers its triple rate pulse. After accumulator 33 delivers the triple rate pulse, normal delivery is resumed through accumulator 33 by switching valve 31 back to accumulator 33 and pressing plunger 47 against reservoir 49 to provide a flow path closer in diameter to conduit 35.

When the time comes to deliver the next test pulse, valve 37 closes the pathway between conduit 35 and conduit 17 and opens the pathway between conduit 41 and conduit 17. After a 3 to 5 second waiting period, the second motor 51 which is also controlled by controller 45 drives plunger 53 against reservoir 55 (which would be full as shown by reservoir 49 in the first accumulator 33) to deliver the test pulse, preferably a triple rate pulse, through conduit 41 to conduit 17. After another waiting period of about 3 to 5 seconds, valve 31 closes the pathway from the flow controller 15 to the first accumulator 33 and opens the pathway to the second accumulator 39.

The first accumulator 33 collects the required volume of fluid for the next triple rate pulse while the second accumulator 39 delivers its test pulse. The normal delivery pattern is then resumed through the second accumulator 39 as described above. The cycle repeats, as needed, for each test pulse to be delivered.

As shown in FIG. 3, the test pulse 57 is in the form of an essentially square wave, preferably having a duration of approximately 3 to 5 seconds, more preferably, four seconds. As described more fully in Bobo Pat. No. 4,648,869 the infusion rate, and hence the volume delivered, during the test pulse preferably varies with the selected infusion rate for the infusion device or controller 15. Specifically, the greater the infusion rate, the greater the volume of fluid delivered for each test pulse. However, the duration of the test pulse 19 may be constant for all selected infusion rates.

The flow controller 15 can be utilized to control the infusion rate prior to and following the test pulse to provide the desired waiting periods but it is more preferable that this function be reserved for the detection device itself. If the flow controller 15 is utilized to control the infusion prior to and following the test pulse, accumulation would occur throughout the normal delivery pattern or a separate source of fluid could be provided for the pulse generator eliminating the need for the accumulator altogether. The embodiments of FIGS. 1 and 2 are preferred because they eliminate the need to involve the infusion device or controller in the infiltration detection process and ensure that the detection device is a stand-alone device capable of being used with any manufacturer's IV pump or a gravity controlled infusion system.

Referring to FIG. 3, the waiting period of reduced or no flow through the detection device provides separating regions just before and just after each test pulse 57, which in this embodiment, are leading and trailing infusion valleys 59 and 61, respectively, contiguous to, and on opposite sides of, the test pulse 57. The normal delivery pattern of the parenteral fluid is shown at 63. The test pulse 57 and the valleys 59 and 61 therefore constitute an altered pattern of flow.

In Bobo's copending application, the valleys 59 and 61 are square waves of short duration during which the infusion rate from the infusion device is reduced sufficiently to wholly or partially compensate for the increased infusion rate which takes place during the test pulse 57. In the present invention, accumulating a portion of the fluid flowing at the selected infusion rate and then delivering that accumulated fluid as the test pulse ensures that a constant average rate of infusion is maintained and no compensation for the increased volume of the test pulse is required. In the present invention, the valleys serve the purpose of providing a quiet period or waiting period in which the baseline is stabilized and noise from the infusion device or controller is eliminated to render better discrimination between test pulse pressure responses and background noise.

Test pulses can be provided in various different ways, and additional examples of test pulses, which can be distinguished from the normal delivery pattern, are shown in FIGS. 3A–3E. Portions of the curves shown in FIGS. 3A–3E corresponding to portions of the curve shown in FIG. 3 are designated by corresponding reference numerals followed by the letters "a", "b", "c", "d", and "e", respectively.

Figure 3A:
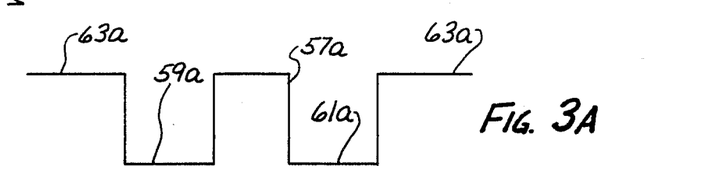

In FIG. 3A, the test pulse 57a is separated from the normal delivery pattern 63a by leading and trailing valleys 59a and 61a in much the same manner as disclosed in FIG. 3. However, the infusion rate during the test pulse 57a is the same as the infusion rate during the normal delivery pattern 63a. Although the infusion rates during the valleys 59a and 61a can be zero, negative, or positive, preferably, the infusion rates during these times are "0" or slightly positive. Also, although the infusion rates during the valleys 59a and 61a can be different, preferably, they are essentially the same.

Figure 3B:
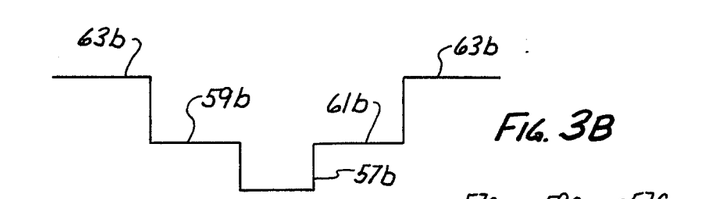

In FIG. 3B, the test pulse 57b is negative, i.e., the pulse generator in the detection device does not deliver accumulated fluid but generates a negative pressure in the conduit. Although the infusion rate during the valleys 59b and 61b may be either positive or negative, in this embodiment, it is essentially zero.

Figure 3C:
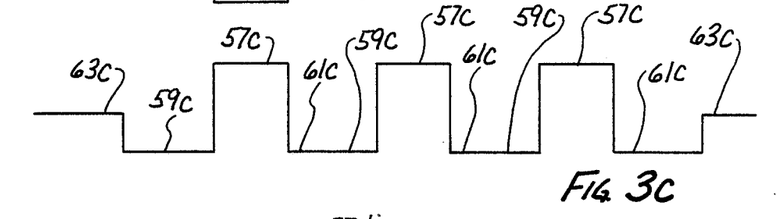

In FIG. 3C, a plurality of test pulses 57c, preferably three, is provided in relatively rapid succession before the infusion rate returns to the normal delivery pattern 63c. In this event, the valleys 59c and 61c between adjacent test pulses 57c constitute both trailing and leading valleys as shown.

Figure 3D:
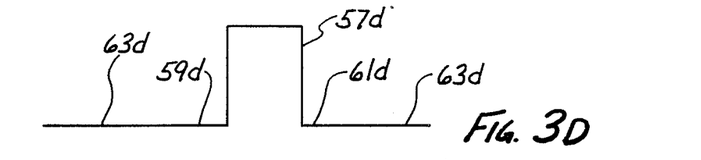

In FIG. 3D, the separating regions 59d and 61d are not distinguishable from the normal delivery pattern 63d, and so the altered pattern of delivery consists only of the test pulse 57d. This can be contrasted with the embodiments described above in which the altered pattern comprises both the leading and trailing separating regions and the test pulses.

Figure 3E:
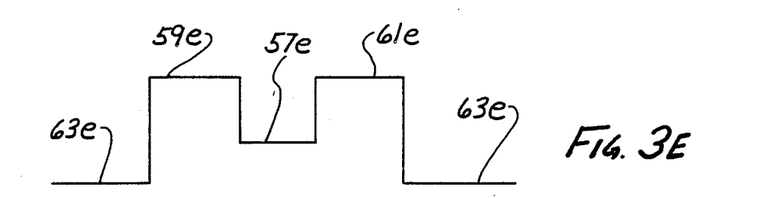

In FIG. 3E, the separating regions 59e and 61e represent periods during which the flow rate is greater than during the normal delivery pattern 63e, and the test pulse 57e represents a decreased flow rate which may be equal to, greater than or less than the flow rate during the normal delivery pattern. As illustrated, the flow rate during the test pulse 57e is greater than the flow rate during the normal delivery pattern 63e. Generally, test pulses of the type shown in FIGS. 3B and 3E, which have flow rates less than the adjacent separating regions, are not preferred.

Figure 4:
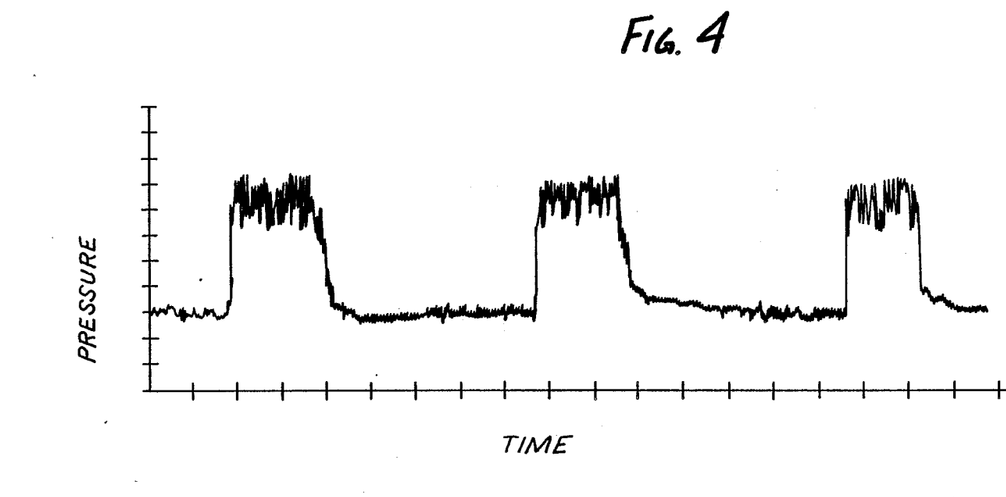
FIG. 4 is a plot showing actual pressure versus time curves representing a triple rate pulse.

FIG. 4 is a plot showing actual pressure versus time curves for the most preferred test pulse delivery pattern, i.e., three sequential test pulses provided in relatively rapid succession. This pressure profile corresponds to the fluid delivery pattern of the test pulse illustrated in FIG. 3C discussed above.

Figure 5:
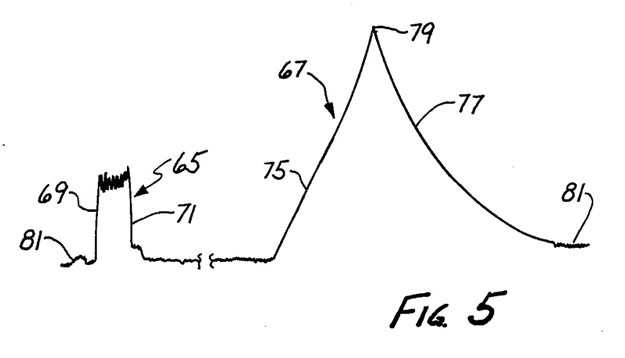
FIG. 5 is a plot showing one pressure wave response indicative of the fluid being properly supplied to the vessel of a patient and a second pressure wave response indicative of infiltration.

The presence of the test pulse 57 in the conduit means 17 creates a pressure wave response which has different characteristics depending upon whether or not the fluid is being improperly supplied by the conduit means 17 to the patient. FIG. 5 shows examples of pressure wave responses 65 and 67 which indicate in-the-vessel and infiltration conditions, respectively. Although the pressure wave responses 65 and 67 are both shown in FIG. 5, they are not in scale in relation to each other. In reality, FIG. 5 shows curves which represent the pressure wave responses, but the curves, if desired, can be considered as the pressure wave responses.

The pressure provided by the pressure wave response 65 rises rapidly and almost instantaneously along a rising edge 69 and decays at about the same rate as represented by a falling edge 71. In between the edges 69 and 71, the pressure remains approximately constant, i.e., the pressure wave response 65 is essentially a square wave. With the open distal end of the needle 18 of the conduit means 17 properly communicating with the interior of the vessel of the patient's cardiovascular system, the pressure wave response 65 is simply the result of forcing the additional fluid into the fluid carried by the vessel. For example, for an infusion rate of 5 cc/hour, the pressure wave response 65 may rise about 5 mm Hg above the base line 81.

When infiltration occurs, the open distal end of the needle 18 is out of the interior of the vessel and communicates with tissue. As a result, the pressure wave response 67 is created in the conduit means 17. Specifically, the pressure wave response 67 rises along a rising edge or leading portion 75 and falls along a falling edge or trailing portion 77 with both the rise time and fall time being much greater than for the pressure wave response 65. In addition, the pressure wave response 67 has a maximum pressure or peak value 79 which is much higher than the maximum pressure or peak value of the pressure wave response 65. For example, for an infusion rate of 5 cc/hour, the pressure wave response 67 may rise about 20 mm Hg above the baseline 81.

The pressure, or pressure response, of the parenteral fluid in the conduit means 17 can be monitored in various different ways, such as by a pressure transducer. The pressure transducer provides an electronic analog pressure signal which is related to the pressure in the conduit means 17. In the two preferred embodiments of the infiltration detection system of the present invention shown in FIGS. 1 and 2, the transducer 81 is contained within the detection device together with the signal conditioning circuitry 87, the A/D converter 89 and the microprocessor 91. The pressure signal from the transducer 85 is conditioned in signal conditioning circuitry 87 and sampled in the analog-to-digital converter (A/D converter) 89 which provides the samples to the microprocessor 91. The signal conditioning circuitry 87 is conventional and is provided for the purpose of adjusting or compensating for various variables, such as temperature. If these variables are not considered significant, the signal conditioning circuitry 87 can be eliminated.

The samples of the pressure signal from the transducer 85 may be taken continuously or taken only during the sample time. In the former case, the microprocessor 91 is used to separate the samples taken during the sample time from those which are not. However, in this embodiment, the A/D converter 89 samples the pressure signal continuously and provides the samples in a digital format to the microprocessor 91.

The sampling frequency of the A/D converter 89 is preferably higher than the sampling frequency required for detecting infiltration or other abnormal infusion. For example, if infiltration detection requires about one sample per second, samples may be taken at, for example, 5 samples per second, 40 samples per second, etc. The samples can then be combined in any of a variety of ways to produce an overall sample value for each second by the microprocessor 91. In any event, the microprocessor 91 performs an integration function as described below to determine if infiltration has occurred.

Figure 6:
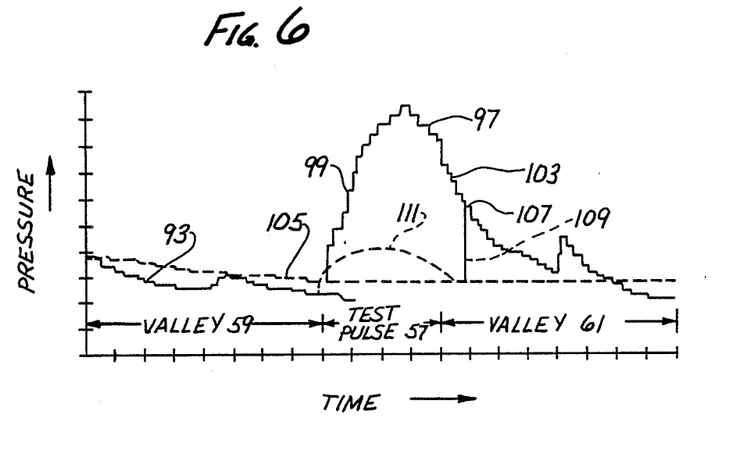
FIG. 6 is a plot showing the relationship of the pressure response to the infusion rate for infiltration conditions and normal conditions at the IV site.

FIG. 6 shows a pressure response 93 in the conduit 17 as measured by the transducer 85 in response to infusion of fluid through the conduit to the patient. As shown, the pressure generally diminishes during the valley 59 until the leading edge of the test pulse 57, at which time a pressure wave response 95 is initiated. The response 95 is indicative of abnormal infusion, e.g., infiltration. The pressure wave response 95 rises, with modest interruption to a peak value 97 of pressure which is reached at approximately the end of the test pulse 57. The pressure then slowly decays during the valley 61, again with modest interruption, to the end of the valley 61. Thus, the pressure wave response 95 has a leading portion 99 that extends from an initial point 101 at the beginning of the test pulse 57 to the peak value 97 and a trailing portion 103 that extends from the peak value 97 to a baseline 105.

The baseline 105 can be established by the microprocessor 91 in various different ways and is preferably a function of the pressure response 93 intermediate test pulses 57. More specifically, the baseline 105 can be established by suitably smoothing the pressure response 93 between test pulses 57, and this function can be carried out by the microprocessor. Accordingly, the baseline 105 lags the pressure response 93. However, at the initiation of the test pulse 57, the baseline 105 then existing is frozen by the microprocessor such that it remains essentially constant throughout at least the test pulse 57 and the trailing valley 61.

Various different techniques can be used to smooth the pressure response 93 between test pulses 57. According to one preferred smoothing technique, the pressure samples from the A/D converter 89 are slew-rate limited and averaged to provide pressure values for updating the baseline 105. By way of illustration and not by way of limitation, the A/D converter 89 may provide 40 pressure samples per second, and the slew-rate limiting processing limits each sample to a value which is no greater than 1.25 times, and no less than 0.75 times, the value of the previous sample. Following this, a $\frac{1}{4}$ second average of ten of the samples is taken, and this average value provides a new point for updating the baseline 105. With this technique, four new smoothed pressure readings are provided each second. The baseline 105 is then typically derived by passing these samples through an additional smoothing process, such as a single-pole low-pass filter with a time constant of about 2 seconds.

A primary advantage of slew-rate limiting is to eliminate spurious spikes that may occur in the pressure response 93 that might be incorrectly interpreted as the peak value 97. In addition, slew-rate limiting and averaging provides a desired smoothing effect for the baseline 105 to reduce transient irregularities that might otherwise occur in the baseline 105.

To determine if infiltration or other abnormal infusion has occurred, the area between the pressure wave response 95 and the baseline 105 is calculated by the microprocessor between the initial point 101 and a truncation point 107. In this embodiment, the truncation point 107 is the time at which the pressure on the trailing portion 103 drops to 50 percent of the peak pressure value 97 observed during the time of increased fluid delivery rate. More generally, the truncation point 107 is the first to occur of a pre-established percent of the peak value 97 and the end of the trailing valley 61. Because in the example of FIG. 6, the predetermined percent of the peak value 97 occurred first, the integration is truncated at this point along a line 109.

Alternatively, or in addition thereto, the integration of the pressure wave response 95 may proceed from the initial point 101 to the peak value 97 to provide a front end area. This front end area may be used in lieu of, or in addition to, the truncated area, i.e., the area obtained from integrating from the initial point 101 to the truncation point 107, to determine whether or not infiltration has occurred.

FIG. 6 also shows a somewhat idealized pressure wave response 111 in dashed lines which is indicative of the proper supply of fluid to the patient. The pressure wave responses 95 and 111 would, of course, not exist simultaneously, but they are shown together for comparative purposes. Applying the same criteria for integration of the pressure wave response 111, virtually the entire area between the pressure wave response 111 and the baseline 105 would be determined. However, this area is much less than the area obtained by the truncated integration of the pressure wave response 95. Accordingly, the microprocessor 91 can readily determine whether or not infiltration has occurred.

The area information can be used in various different ways to arrive at a decision regarding the presence or absence of infiltration or other abnormal infusion. For example, both the truncated area and the front end area may be normalized and compared with known thresholds, and an alarm condition may be declared in response to one or more of these areas exceeding the established threshold. In a preferred decision-making technique, an alarm condition is not declared until three consecutive normalized truncated areas or three consecutive normalized front end areas resulting from three consecutive test pulses have exceeded their respective thresholds.

More specifically, in one technique, the truncated area is normalized by dividing it by a divisor which is a function of the difference between the infusion rate during the test pulse and the infusion rate during either of the valleys 59 and 61. Preferably, the function is simply the difference between these infusion rates. The quotient or normalized area is then compared with a known threshold. The front end area is normalized in the same way and compared with its threshold.

It has been found that the threshold may vary with a number of factors, for example, the gauge or size of the needle 18. The areas can be effectively normalized for needle (or other cannula) size by employing different thresholds for different ranges of needle size. Suitable thresholds for both truncated area and front end area as a function of needle gauge can be obtained by using human, animal and/or laboratory models of infiltration.

The normalization for rate, needle size, and other factors may not be important when delivering a triple rate pulse, since the three pressure responses occur close in time and share the same rate, needle size and other system variables. The relative change in area between successive rate pulses in a triple rate pulse should be directly indicative of IV complication without the need for additional normalization. Thus, the triple rate pulse has the advantage of being essentially self normalizing.

Another feature of this invention is to ascertain if pressure conditions in the conduit means 17 are suitable for detecting if fluid is being improperly supplied by the conduit means to the patient. Although this feature of the invention is particularly adapted for use with the integration technique of this invention, its use is not so limited, and it can be used with other techniques for determining whether or not abnormal infusion exists.

The suitability of the pressure conditions in the conduit means 17 can be evaluated in various different ways to determine if these conditions are suitable for detecting abnormal infusion. This can be accomplished, for example, by comparing a function of the pressure of the fluid in the conduit means 17 during the normal delivery pattern 63 to a threshold. Although the function of the pressure of the fluid in the conduit means 17 can be the raw pressure samples from the A/D converter 89 per se, preferably this function includes some form of smoothing.

According to a preferred technique, the following equation is used:

$$BQI = B1 + K(B2)$$

where, BQI is a baseline quality index, B1 is the magnitude of the baseline 105 (FIG. 6) prior to the valley 59, K is a constant which may be, for example, 3 and B2 is the rms value of a plurality, such as 120, of baseline 105 magnitudes occurring just prior to the baseline magnitude representing B1. Thus, BQI is a function of the pressure in the conduit means 17. Assuming that the pressure response 95 is slew-rate limited, averaged and low-pass filtered to determine the baseline 105 as described above, then B1 is the last baseline 105 value prior to the valley 59, and B2 is the rms value of 120 baseline values immediately preceding the value used for determining B1.

It has been found that, if BQI as calculated using the equation set forth above exceeds a threshold, the pressure conditions in the conduit means 17 are not suitable for determining whether or not abnormal infusion exists. Although this threshold can be adjusted as desired, by way of example, a threshold of 85 mmHg is suitable for many applications.

Figure 7A:
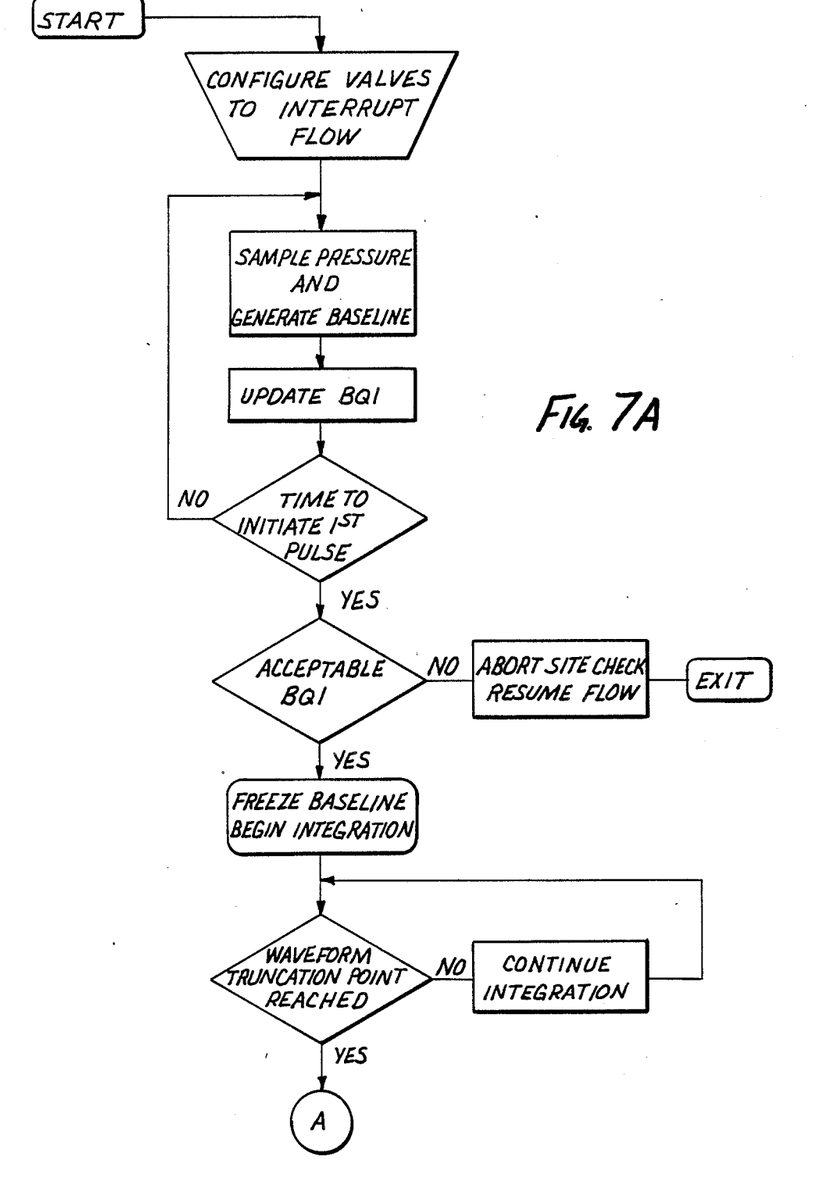
FIG. 7 is a flow chart showing how the system functions to detect infiltration.
Figure 7B:
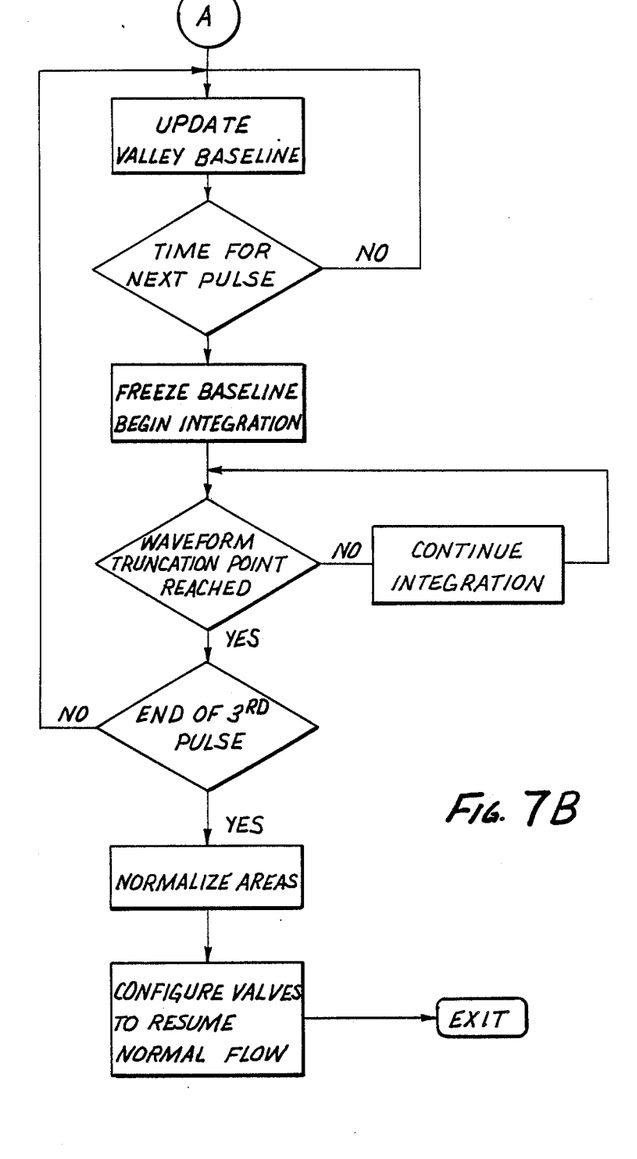

FIG. 7 is a flow chart showing the basic steps in a preferred embodiment of the infiltration detection method of the present invention. According to the preferred embodiment, three test pulses are generated in sequence and their respective pressure wave response curves are integrated and averaged. The first step is to configure the valves in the accumulator to interrupt the flow to the patient or to reduce the flow to provide the waiting period prior to delivery of the test pulse.

During the waiting period, the next step is to sample the pressure in the conduit means 17 and generate a baseline. The BQI is then calculated using the equation set out above. When the time comes to initiate the first test pulse, it is allowed to proceed only if the BQI is acceptable, i.e., below the threshold magnitude as described above. If the BQI is above the threshold magnitude, the site check is aborted and the normal delivery pattern is resumed.

If the BQI is acceptable, the baseline is frozen, the test pulse is delivered, and the integration between the baseline and the pressure response curve begins simultaneously. The integration continues from the initial point to the truncation point, preferably the first to occur of a pressure less than 50 percent of the peak value or the end of the trailing valley. Following the test pulse and integration of the resulting pressure response curve, another waiting period or valley of reduced or no flow is provided. The baseline is then updated and when the time comes for the second test pulse, if the baseline is acceptable based on the BQI calculation, the baseline is frozen, a second test pulse is delivered and the resulting pressure wave response curve is integrated simultaneously from the initial point to the truncation point.

The sequence is then repeated to deliver a third test pulse and integrate the resulting pressure wave response curve. At the end of the integration of the third test pulse, the truncated areas of the three test pulse pressure response curves are normalized for infusion rate and needle-size effects as described above. The microprocessor 91 then makes a decision concerning abnormal infusion as described above, and if infusion is abnormal, the alarm 113 is energized and/or infusion is terminated until the condition at the IV site can be corrected.

The abnormal infusion may be the result of any condition, such as infiltration, occlusion of the conduit means 17, clotting or phlebitis, which leads to the creation of the pressure wave response 95 (FIG. 6). In any event, once the abnormal infusion is declared, an attendant can determine the particular cause and seek to remedy it.

Although an exemplary embodiment of the invention has been shown and described, many changes, modifications and substitutions may be made by one having ordinary skill in the art without necessarily departing from the spirit and scope of this invention.

What is claimed is:

1. An apparatus for detecting whether a fluid is being properly supplied to a patient through conduit means by a flow controller which is located upstream from the detection apparatus and which infuses fluid in a normal delivery pattern at any of a plurality of selected infusion rates through conduit means to the patient, comprising:
   (a) means for diverting and accumulating a predetermined volume of the upstream flow from the flow controller for use as a test pulse;
   (b) means for delivering the test pulse of the fluid through the conduit means to the patient with the test pulse being distinguishable from the normal delivery pattern and with the test pulse creating a pressure wave response in the conduit means;
   (c) means for determining the area between a baseline and at least a portion of a pressure versus time curve representing the pressure wave response; and
   (d) means responsive to the magnitude of said area for detecting if the fluid is being improperly supplied by the conduit means to the patient.

2. A detection device for detecting whether a fluid is being properly supplied to a patient through conduit means by a flow controller, the flow controller being of the type that infuses fluid in a normal delivery pattern at any of a plurality of selected infusion rates, wherein:
   said detection device is located between said flow controller and the patient and operates independently of said flow controller, and said detection device comprises (a) means for diverting at least a portion of the fluid flowing from the flow controller through the conduit means prior to delivery of a fluid test pulse, (b) means for delivering said test pulse through the conduit means to the patient, said test pulse being distinguishable from the normal delivery pattern of the flow controller and said test pulse creating a pressure wave response in the conduit means, (c) means for determining the area between a base line and at least a portion of a pressure versus time curve representing the pressure wave response, and (d) means responsive to the magnitude of said area for detecting if the fluid is being improperly supplied by the conduit means to the patient.

3. An apparatus according to claim 2, wherein the pressure wave response has a peak value of pressure and a leading portion and a trailing portion on opposite sides of the peak value and said determining means determines the area from an initial point on the leading portion side of the peak value to a truncation point with the truncation point being on a portion of said curve corresponding to the trailing portion of the pressure wave response.

4. An apparatus according to claim 3, wherein said truncation point is essentially outside the noise range.

5. An apparatus according to claim 3, wherein said determining means establishes the truncation point as a percent of the peak value.

6. An apparatus according to claim 3, wherein said truncation point is at a time at which the pressure is no more than about 30 percent of the peak value.

7. An apparatus according to claim 3, wherein said truncation point is at a time at which the pressure is no less than about 70 percent of the peak value.

8. An apparatus according to claim 3, wherein said truncation point is at a time at which the pressure is between about 30 percent to about 70 percent of the peak value.

9. An apparatus according to claim 3, wherein said truncation point is at a time at which the pressure is about 50 percent of the peak value.

10. An apparatus according to claim 3, wherein the initial point is essentially at the beginning of the point on said curve corresponding to the beginning of the pressure wave response.

11. An apparatus according to claim 3, wherein said test pulse delivery means delivers the fluid in an altered pattern, said altered pattern including a test pulse and leading and trailing separating regions on opposite sides of the test pulse, each of which provides a different flow rate of fluid than the adjacent portions of the test pulse.

12. An apparatus according to claim 11, wherein said altered pattern includes at least three test pulses delivered in rapid succession and leading and trailing separating regions on opposite sides of each test pulse.

13. An apparatus according to claim 12, wherein said determining means establishes the truncation point as the first to occur of a percent of peak value and said trailing separating region.

14. An apparatus according to claim 12, wherein the detecting means includes means for comparing the area of each test pulse to determine the relative change in area between each successive test pulse, said change being indicative of a fluid being improperly supplied by the conduit means to the patent, thereby making the triple rate pulse essentially self-normalizing.

15. An apparatus according to claim 11, wherein the test pulse provides a greater flow rate of fluid than the normal delivery pattern and the separating regions are valleys each of which provide a lesser flow rate of fluid than said adjacent portions of the test pulse.

16. An apparatus according to claim 11, wherein the detecting means includes means for dividing said area by a divisor which is a function of the difference between the flow rate during at least one of the valleys and the test pulse to provide a quotient and means for comparing the quotient to a threshold.

17. An apparatus according to claim 2, including means for establishing the baseline as essentially constant for the determination of said area.

18. An apparatus according to claim 2, including means for determining the baseline for use in the determination of said area as a function of the pressure in the conduit means when the pressure wave response is not present.

19. An apparatus according to claim 2, including first means responsive to the pressure of the fluid in the conduit means during the normal delivery pattern to ascertain if pressure conditions in the conduit means are suitable for detecting whether the fluid is being improperly supplied by the conduit means to the patient.

20. An apparatus according to claim 19, wherein said first means includes means for comparing a function of the pressure of the fluid in the conduit means during the normal delivery pattern to a threshold to ascertain if pressure conditions in the conduit means are suitable for detecting if fluid is being improperly supplied by the conduit means to the patient.

21. An apparatus according to claim 20, wherein said function of the pressure equals $B1 + K(B2)$ where B1 is the baseline pressure at an instant prior to the test pulse, K is a constant and B2 is the rms value of a plurality of segments of the baseline pressure prior to the test pulse and with at least one of said segments being prior to said instant.

22. An apparatus according to claim 2, including means for establishing the baseline including means for averaging the pressure in the conduit means during at least a portion of the time that the pressure wave response is not present.

23. An apparatus according to claim 2, including means for establishing the baseline including means for sampling the pressure in the delivery system during at least a portion of the time that the pressure wave response is not present to provide a plurality of samples, means for averaging said samples and means for excluding from said average at least the portion of any of said samples that exceeds a threshold.

24. An apparatus according to claim 2, wherein said detecting means includes means for normalizing said area and comparing the normalized area to a threshold.

25. An apparatus according to claim 2, wherein the pressure wave response has a peak value of pressure and a leading portion and a trailing portion on opposite sides of the peak value and said determining means determines the area from an initial point on the leading portion side of the peak value to about the peak value of pressure.

26. An apparatus according to claim 25, wherein the area between the initial point and about the peak value is a front end area and the determining means also determines a truncated area between the initial point and a truncation point with the truncation point being on a portion of said curve corresponding to the trailing portion of the pressure wave response and said detecting means is responsive to said front end area and said truncated area to detect if the fluid is being improperly supplied by the conduit means to the patient.

27. A detection device for detecting whether a fluid is being properly supplied to a patient through conduit means by a flow controller, the flow controller being of the type that infuses fluid in a normal delivery pattern at any of a plurality of selected infusion rates, wherein:

said detection device is located between said flow controller and the patient and operates independently of said flow controller, and said detection device comprises (a) means for diverting at least a portion of the fluid flowing from the flow controller through the conduit means prior to delivery of a fluid test pulse, (b) means for delivering said test pulse through the conduit means to the patient, said test pulse being distinguishable from the normal delivery pattern of the flow controller and said test pulse creating a pressure wave response in the conduit means, and (c) means responsive to the pressure wave response in the conduit means for detecting if the fluid is being improperly supplied by the conduit means to the patient.

28. An apparatus according to claim 27, further comprising means responsive to the selected flow rate of the flow controller for controlling the flow rate of the fluid provided during the test pulse, whereby said controlling means decreases the ratio of test pulse flow rate to selected flow rate for increased selected flow rates, and said detecting means includes means responsive to the rate of change of the pressure wave response in the conduit means for detecting whether the fluid is being improperly supplied by the conduit means to the patient.

29. An apparatus according to claim 27, wherein said test pulse delivery means includes means for selectively initiating a test pulse on demand.

30. An apparatus according to claim 27, wherein said detecting means includes means responsive to the rate of change of at least a portion of the pressure wave response in the conduit means for detecting whether the fluid is being improperly supplied by the conduit means to the patient.

31. An apparatus according to claim 27, wherein said detecting means detects the improper supply of the fluid when the pressure change of at least a portion of the pressure wave response exceeds a predetermined magnitude.

32. An apparatus according to claim 27, wherein said detecting means includes a pressure transducer for providing a pressure signal which is related to the pressure in the conduit means, means for sampling said pressure signal at least during a sample time which occurs at least partially during the pressure wave response to provide a plurality of digital samples and means responsive to the samples obtained during said sample time for detecting whether the fluid is being improperly supplied by the conduit means to the patient.

33. An apparatus according to claim 27, wherein said detecting means is responsive at all infusion rates of the infusion device to the change in pressure of the same portion of the pressure wave response during a predetermined period for detecting if the fluid is being improperly supplied to the patient.

34. An apparatus according to claim 27, further comprising means responsive to the detecting means for indicating that the fluid is not being properly supplied to the patient by the conduit means.

35. A detection device according to claim 2 or 27, further comprising means for accumulating a predetermined volume of said fluid for use as the test pulse.

36. A detection device according to claim 2 or 27, further comprising means for providing reduced fluid flow or no fluid flow prior to delivery of said test pulse to permit the baseline to stabilize prior to delivery of said test pulse.

37. A detection device according to claim 2 or 27, wherein said diverting means diverts substantially all of the fluid flowing from the flow controller prior to delivering a test pulse.

38. A detection device according to claim 2 or 27, wherein said diverting means diverts said fluid flowing from the flow controller prior to and during delivery of said test pulse.

39. A detection device according to claim 36, wherein said diverting means diverts said fluid flowing from the flow controller prior to and during delivery of said test pulse.

40. A detection device according to claim 2 or 27, wherein said test pulse delivery means alters the normal delivery pattern by delivering a test pulse at an increased flow rate and providing a period of reduced or no flow prior to and following delivery of said test pulse.

41. An apparatus for detecting whether a fluid is being properly supplied to a patient by conduit means from a flow controller which is located upstream from the detection apparatus and which infuses fluid in a normal delivery pattern at any of a plurality of selected infusion rates through conduit means to the patient, comprising:
 (a) means for diverting and accumulating a predetermined volume of the upstream flow from the flow controller for use as a test pulse;
 (b) means for delivering said test pulse of the fluid through the conduit means to the patient with the test pulse being distinguishable from the normal delivery pattern, said test pulse creating a pressure wave response in the conduit means; and
 (c) means responsive to the pressure wave response in the conduit means for detecting whether the fluid is being improperly supplied by the conduit means to the patient.

42. An apparatus according to claim 41, wherein the test pulse is delivered at an increased flow rate greater than the flow rate during normal delivery pattern, and the test pulse delivery means includes means for delivering a reduced flow rate of fluid or no flow of fluid adjacent the test pulse.

43. An apparatus according to claim 42, wherein said delivery means provides reduced flow or no flow on opposite sides of the test pulse, with said reduced flow rate being less than the flow rate during the normal delivery pattern.

44. A method for detecting whether a fluid is being properly supplied to a patient by conduit means from a flow controller which infuses fluid in a normal delivery pattern at any of a plurality of selected infusion rates through conduit means to the patient, comprising the steps of:
 (a) diverting and accumulating a predetermined amount of the upstream flow from the flow controller for use as a test pulse of fluid;
 (b) delivering said test pulse through the conduit means to the patient from a point downstream from the flow controller, with the test pulse being distinguishable from the normal delivery pattern and with the test pulse creating a pressure wave response in the conduit means; and
 (c) monitoring at least a portion of the pressure wave response in the conduit means to detect whether the fluid is being improperly supplied by the conduit means to the patient.

45. A method for detecting whether a fluid is being improperly supplied to a patient by conduit means from a flow controller which infuses fluid in a normal delivery pattern at any of a plurality of selected infusion rates through conduit means to the patient, comprising:
  (a) diverting and accumulating a predetermined volume of the upstream flow from the flow controller for use as a test pulse;
  (b) delivering said test pulse through the conduit means to the patient, with the test pulse being distinguishable from the normal delivery pattern and with the test pulse creating a pressure wave response in the conduit means;
  (c) determining the area between a base line and at least a portion of a pressure versus time curve representing the pressure wave response; and
  (d) using the magnitude of said area to detect whether the fluid is being improperly supplied by the conduit means to the patient.

46. A method for detecting whether a fluid is being improperly supplied to a patient by conduit means from a flow controller which infuses fluid in a normal delivery pattern at any of a plurality of selected infusion rates through conduit means to the patient, comprising the steps of:
  (a) diverting at least a portion of the upstream flow of fluid from the flow controller prior to delivery of a fluid test pulse;
  (b) delivering said test pulse through the conduit means to the patient at a point downstream from the flow controller, said test pulse being distinguishable from the normal delivery pattern of the flow controller and said test pulse creating a pressure wave response in the conduit means; and
  (c) monitoring at least a portion of the pressure wave response in the conduit means to detect whether the fluid is being improperly supplied by the conduit means to the patient.

47. A method for detecting whether a fluid is being improperly supplied to a patient by conduit means from a flow controller which infuses fluid in a normal delivery pattern at any of a plurality of selected infusion rates through conduit means to the patient, comprising the steps of:
  (a) diverting at least a portion of the upstream flow of fluid from the flow controller prior to delivery of a fluid test pulse;
  (b) delivering said test pulse through the conduit means to the patient at a point downstream from the flow controller, said test pulse being distinguishable from the normal delivery pattern of the flow controller and said test pulse creating a pressure wave response in the conduit means;
  (c) determining the area between a base line and at least a portion of a pressure versus time curve representing the pressure wave response; and
  (d) monitoring the magnitude of said area to detect whether the fluid is being improperly supplied by the conduit means to the patient.

48. A method according to claim 46 or 47, further comprising the step of accumulating a predetermined volume of said fluid for use as the test pulse.

49. A method according to claim 46 or 47, further comprising the step of providing reduced fluid flow or no fluid flow prior to delivery of said test pulse to permit the base line to stabilize prior to delivery of said test pulse.

50. A method according to claim 46 or 47, wherein said diverting step diverts substantially all of the fluid flowing from the flow controller prior to delivering a test pulse.

51. A method according to claim 46 or 47, wherein said diverting step diverts said fluid flowing from the flow controller prior to and during delivery of said test pulse.

52. A method according to claim 50, wherein said diverting step diverts said fluid flowing from the flow controller prior to and during delivery of said test pulse.

53. A method according to claim 46 or 47, wherein said test pulse delivery step alters the normal delivery pattern by delivering a test pulse at an increased flow rate and providing a period of reduced or no flow prior to and following delivery of said test pulse.

* * * * *